US012564667B2

(12) United States Patent
  Gao

(10) Patent No.: US 12,564,667 B2
(45) Date of Patent: Mar. 3, 2026

(54) DEVICES CONTAINING CELLULAR MEMBRANE AND USES THEREOF

(71) Applicant: Arytha Biosciences LLC, San Diego, CA (US)

(72) Inventor: Weiwei Gao, San Diego, CA (US)

(73) Assignee: Arytha Biosciences LLC, San Diego, CA (US)

(*) Notice: Subject to any disclaimer, the term of this patent is extended or adjusted under 35 U.S.C. 154(b) by 201 days.

(21) Appl. No.: 17/793,338

(22) PCT Filed: Jan. 18, 2021

(86) PCT No.: PCT/US2021/013833
  § 371 (c)(1),
  (2) Date: Jul. 15, 2022

(87) PCT Pub. No.: WO2021/150460
  PCT Pub. Date: Jul. 29, 2021

(65) Prior Publication Data
  US 2023/0051094 A1      Feb. 16, 2023

Related U.S. Application Data

(60) Provisional application No. 62/963,465, filed on Jan. 20, 2020.

(51) Int. Cl.
  *A61M 1/36*      (2006.01)
  *A61M 1/34*      (2006.01)

(52) U.S. Cl.
  CPC ......... *A61M 1/3679* (2013.01); *A61M 1/3489* (2014.02)

(58) Field of Classification Search
  CPC ........ A61M 1/34; A61M 1/16; A61M 1/3679; A61M 1/3482; A61M 1/3486;
  (Continued)

(56) References Cited

U.S. PATENT DOCUMENTS 5,858,238 A * 1/1999 McRea ................ B01D 61/145
                                                        210/651
6,673,285 B2    1/2004 Ma
                (Continued)

FOREIGN PATENT DOCUMENTS

CN      101559246 A    10/2009
CN      106163504 A    11/2016
                (Continued)

OTHER PUBLICATIONS

International App. No. PCT/US2021/013833; International Search Report mailed Mar. 25, 2021.
(Continued)

*Primary Examiner* — Susan S Su
*Assistant Examiner* — Erin A Kim

(57)      ABSTRACT

The present disclosure relates to devices, e.g, extracorporeal blood purification (EBP) devices, which comprise a cartridge or sorbent comprising a cellular membrane derived from a cell. The present disclosure also relates methods for removing or reducing a substance, e.g, an undesirable substance, from a fluid, e.g, a subject's blood, using the devices or EBP devices.

23 Claims, 3 Drawing Sheets

Figure 1:
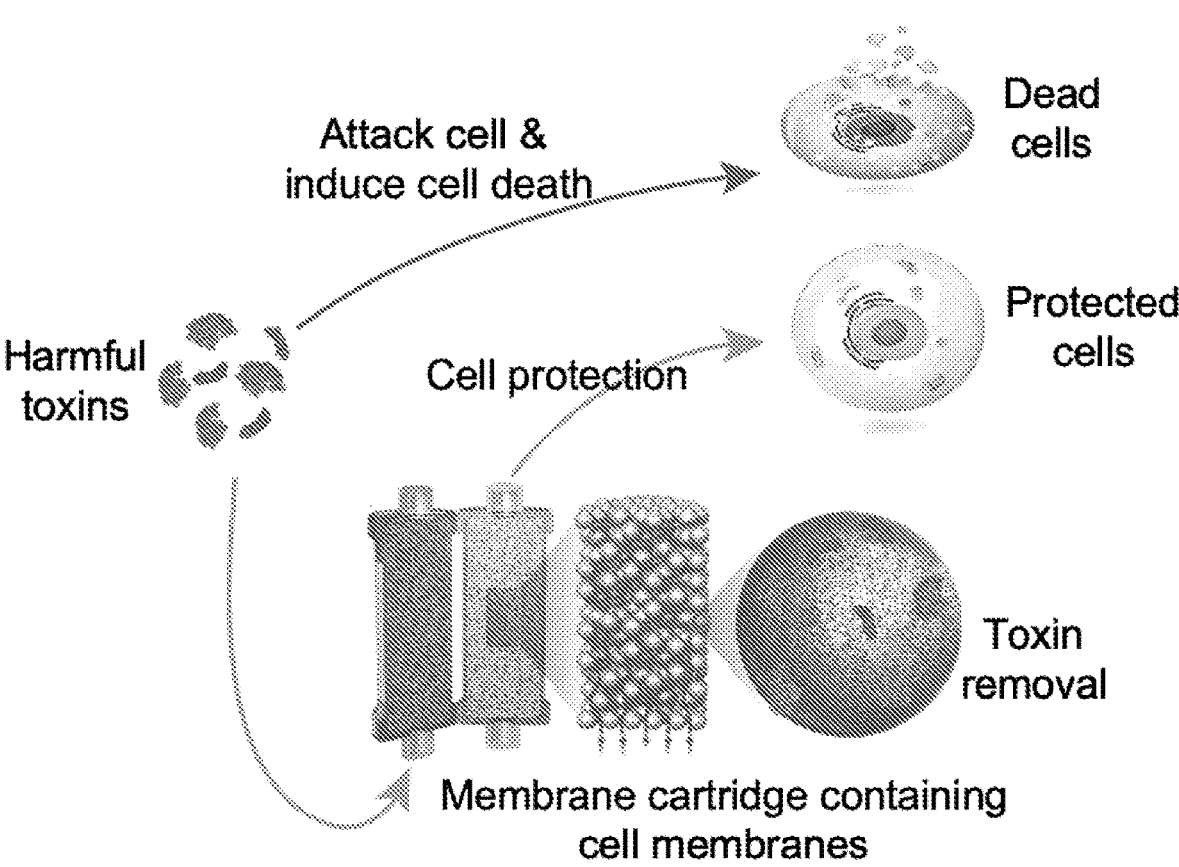

(58) Field of Classification Search
CPC ............. A61M 1/3489; B01D 2313/68; B01D
67/00412; C12M 25/02
See application file for complete search history.

(56) References Cited

U.S. PATENT DOCUMENTS

| | | | |
|---|---|---|---|
| 11,000,593 B2 | 5/2021 | Zhang et al. | |
| 11,359,058 B2 | 6/2022 | Gao et al. | |
| 12,097,290 B2 | 9/2024 | Zhang et al. | |
| 2011/0208106 A1* | 8/2011 | Levin ...................... | A61M 1/34 |
| | | | 604/6.04 |
| 2011/0263022 A1 | 10/2011 | Krause et al. | |
| 2015/0157570 A1 | 6/2015 | Babiychuk et al. | |
| 2016/0312298 A1 | 10/2016 | Ting et al. | |
| 2017/0079909 A1* | 3/2017 | Zhang ................... | A61L 26/008 |
| 2017/0181426 A1 | 6/2017 | Wolf et al. | |
| 2017/0274059 A1 | 9/2017 | Zhang et al. | |
| 2022/0221464 A1 | 7/2022 | Zhang et al. | |
| 2022/0362162 A1 | 11/2022 | Gao et al. | |

FOREIGN PATENT DOCUMENTS

| | | |
|---|---|---|
| CN | 115768499 A | 3/2023 |
| JP | 2017528253 A | 9/2017 |
| JP | 2023-511333 A | 3/2023 |
| WO | 2012103025 A2 | 8/2012 |
| WO | 2015/021390 A2 | 2/2015 |
| WO | 2016048901 A1 | 3/2016 |
| WO | 2017027760 A1 | 2/2017 |
| WO | 2017120342 A1 | 7/2017 |

OTHER PUBLICATIONS

Gong et al., Biomembrane-Modified Field Effect Transistors for Sensitive and Quantitative Detection of Biological Toxins and Pathogens, ACS Nano, vol. 13, Mar. 4, 2019 [retrieved on Mar. 11, 2021]. Retrieved from the Internet: <URL: https://pubs.acs.org/doi/10.1021/acsnano.9b00911 >. pp. 3714-3722.
International App. No. PCT/US2021/013833; IPRP issued Jul. 26, 2022.
International App. No. PCT/US2021/013833; Written Opinion mailed Mar. 25, 2021.
European Patent Application 21 743 975.1; Extended European search report.
European Patent Application 21 743 975.1; communication under Rule 70(2) EPC.
European Patent Application 21 743 975.1; Response to communication under Rule 70(2) EPC.
European Patent Application 21 743 975.1; marked-up claims.
JP Appl. No. 2022-543680; Request for Examination.
JP Appl. No. 2022-543680; Voluntary Amendment.
JP Appl. No. 2022-543680; Official Action dated Oct. 15, 2024.
JP Appl. No. 2022-543680; English Translation of Official Action.
JP Appl. No. 2022-543680; Argument in response to the Official Action dated Oct. 15, 2024.
JP Appl. No. 2022-543680; Amendment in response to the Official Action dated Oct. 15, 2024.
JP Appl. No. 2022-543680; Amended claims in Response to the Official Action dated Oct. 15, 2024.
Wansong Chen et al., "Coating nanofiber scaffolds with beta cell membrane to promote cell proliferation and function," Nanoscale, 8:10364-10370 (2016).
Notice of Allowance, Japanese Patent Application No. 2022-543680.
CN Application No. 202180013335.5; Response to the first office action filed on Aug. 25, 2025.
Rao et al (Adv Funct Mater. Jul. 2018. 28: 1803531, p. 1-9 and Supporting Information, 28 pages).
Genomic Medicine, Feb. 1, 2019, 4:2, 1-11 to Fan et al. (hereinafter "Fan").
Nature Biotechnology, Aug. 30, 2012(8): 777-782 and Online Methods, 2 pages to Ramskold, et al. (hereinafter "Ramskold").
Non-Final Office Action dated Feb. 7, 2025 for U.S. Appl. No. 17/607,200.
Response to the Non-Final Office Action dated Jun. 5, 2025 for U.S. Appl. No. 17/607,200.
Final Office Action dated Jul. 14, 2025 for U.S. Appl. No. 17/607,200.
First Office Action for Chinese Application No. 202180013335.5.
English translation of the First Office Action for Chinese Application No. 202180013335.5.
CN Application No. 202180013335.5; Second Office Action dated Oct. 14, 2025.
The communication according to Rule 71(3) EPC for European Patent Application 21 743 975.1.

* cited by examiner

DEVICES CONTAINING CELLULAR MEMBRANE AND USES THEREOF

I. RELATED APPLICATION

The present application is a national stage application of International Patent Application Serial No. PCT/US2021/013833, filed on Jan. 18, 2021, entitled "DEVICES CONTAINING CELLULAR MEMBRANE AND USES THEREOF," which claims priority to U.S. provisional patent application No. 62/963,465, filed on Jan. 20, 2020. The disclosures and contents of the above-referenced applications are incorporated herein by reference in their entireties for all purposes.

II. FIELD OF THE INVENTION

The present disclosure relates to devices, e.g., extracorporeal blood purification (EBP) devices, which comprise a cartridge or sorbent comprising a cellular membrane derived from a cell. The present disclosure also relates to methods for removing or reducing a substance, e.g., an undesirable substance, from a fluid, e.g., a subject's blood, using the devices or EBP devices.

III. BACKGROUND OF THE INVENTION

Extracorporeal blood purification (EBP) is a treatment procedure of which a patient's blood is allowed to pass through a device for the removal of undesirable solutes such as waste products, proinflammatory cytokines, and toxins. Devices used for EBP can be divided into two major categories: (1) filtration based on molecule sizes, such as such as hemodialysis (HD), hemofiltration (HF), hemodiafiltration (HDF) and high-flux dialysis (HFD), and (2) adsorption, such as devices based on non-specific physical interactions or specific ligand-receptor binding interactions. Due to its convenient and low risk of complications, EBP has been used to treat critical diseases such as renal failure, liver failure, and sepsis.

However, existing technologies face significant drawbacks. (1) Devices based on filtration, convection, and diffusion use molecule weight as the cut-off, unable to distinguish the biological identity of the filtrates. (2) Convection and diffusion cannot achieve good clinical clearances for high-molecular-weight and hydrophobic molecules owing to the limited volume of infusion in convection and limited membrane permeability in diffusion. (3) Devices based on physical adsorption such as charcoal are non-specific and create harm by non-differentially removing vital molecules. (4) For specific adsorption, choices of ligands that bind with the toxins are limited and costly. For each target toxin, the ligand needs to be specifically produced, which is impractical for diseases where most pathological factors or virulence factors are unknown.

Novel devices or EBP devices and methods for removing or reducing a substance, e.g., an undesirable substance, from a subject's liquid or blood using the devices or EBP devices to address the challenges of the current devices and methods are needed. The present invention addresses this and the related needs in the art.

IV. SUMMARY OF THE INVENTION

In one aspect, the present disclosure provides for a device, e.g., an extracorporeal blood purification (EBP) device, which comprises a cartridge or sorbent comprising a cellular membrane derived from a cell.

In another aspect, the present disclosure provides a device assembly that comprises at least two of the above described devices or EBP devices that are in fluid communication. The devices or EBP devices in the device assembly comprise cartridges or sorbents comprising cellular membranes derived from different types of cells.

In still another aspect, the present disclosure provides a method for removing or reducing a substance (e.g., an undesirable substance) from a fluid, e.g., a subject's blood, which method comprises, ex vivo, contacting a fluid, e.g., a subject's blood, with a device comprising a cellular membrane derived from a cell. In some embodiments, the present methods comprise, ex vivo, contacting a fluid, e.g., a subject's blood, with a device or an EBP device that comprises a cartridge or sorbent comprising a cellular membrane derived from a cell. In some embodiments, the present methods comprise, ex vivo, contacting a fluid, e.g., a subject's blood, with a device assembly that comprises at least two of the above described devices or EBP devices that are in fluid communication.

In some aspects, the prevent disclosure relates to U.S. application Ser. No. 13/827,906, filed Mar. 14, 2013, and published as US 2013/0337066 A1, International Application No. PCT/US2012/039411, filed May 24, 2012 and published as WO 2013/052167 A2 and International Application No. PCT/US2017/012342, filed Jan. 5, 2017 and published as WO 2017/120342 A1. The contents of the above applications are incorporated by reference in their entireties.

V. BRIEF DESCRIPTION OF THE DRAWINGS

Those of skill in the art will understand that the drawings, described below, are for illustrative purposes only. The drawings are not intended to limit the scope of the present teachings in any way.

FIG. 1 illustrates using cell membrane as the component for extracorporeal detoxification.

Figure 2:
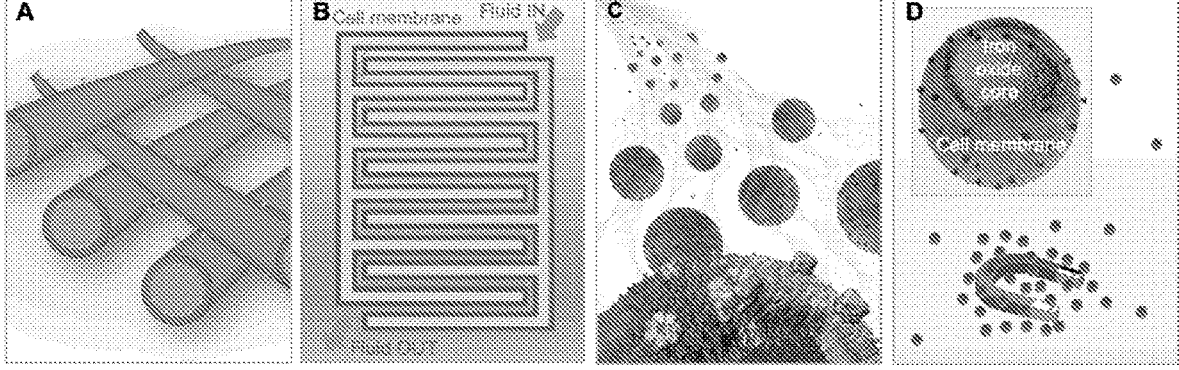

FIG. 2 illustrates examples of packing cell membrane to make "membrane cartridges" for extracorporeal detoxification, including (A) cell membrane wrapped around nanofibers, (B) cell membrane spread onto plates for detoxification, (C) cell membrane formed into vesicles or particles and embedded inside hydrogel gel for detoxification, and (D) cell membrane wrapped around magnetic particles for enrichment and isolation during the detoxification.

Figure 3:
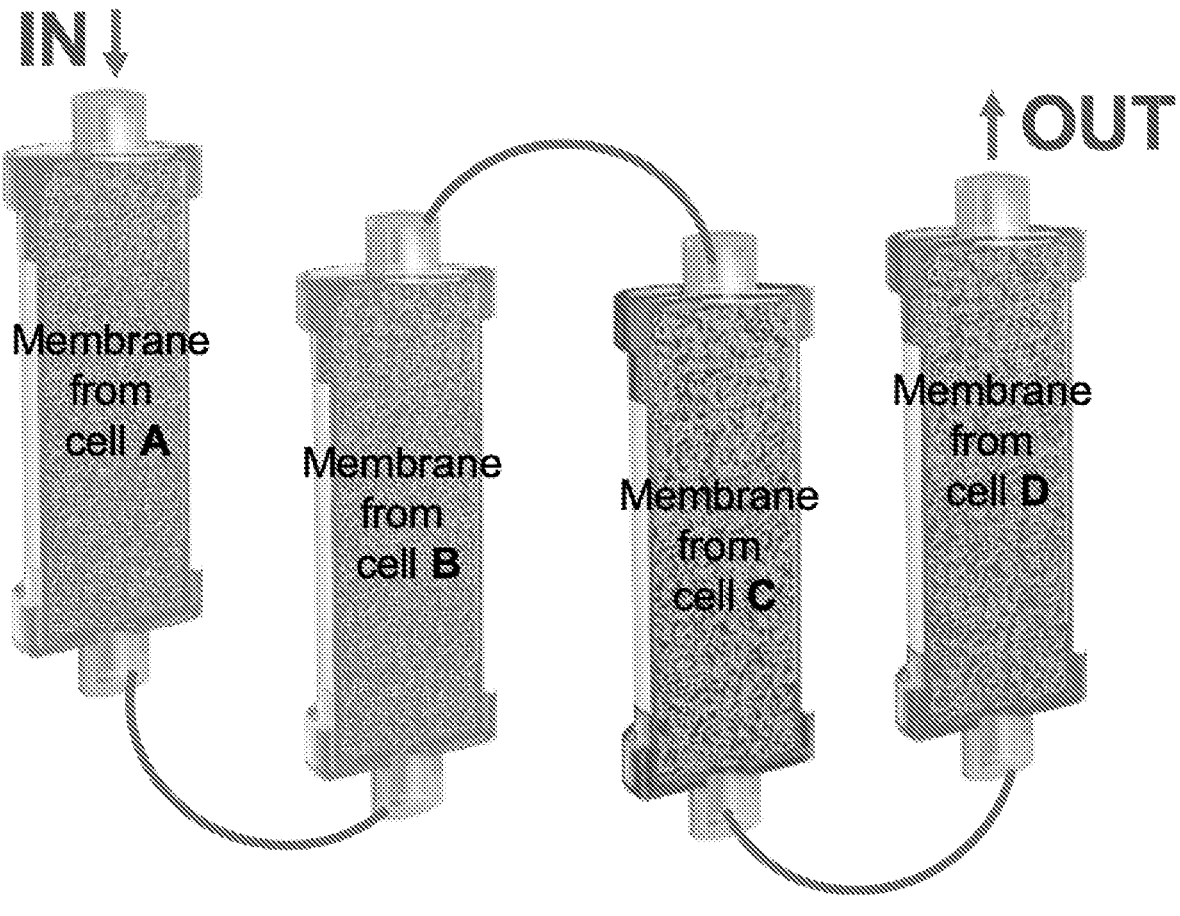

FIG. 3 illustrates an exemplary device assembly wherein cell membrane cartridges are serially connected. A fluid, e.g., a subject's blood, can go through the cell membrane cartridges for sequential detoxification or substance removal.

VI. DETAILED DESCRIPTION OF THE INVENTION

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, 20$^{th}$ ed., (Lippincott, Williams & Wilkins 2003), and Remington, The Science and Practice of Pharmacy, 22$^{th}$ ed., (Pharmaceutical Press and Philadelphia College of Pharmacy at University of the Sciences 2012).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. DEFINITIONS

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell and the prepared or isolated membrane can be combined with other substances or materials to form a derived membrane. In another example, a cell can be recombinantly engineered to produce "non-natural" substances that are incorporated into its membrane in vivo, and the cellular membrane can be prepared or isolated from the cell to form a derived membrane.

In various embodiments, the cellular membrane covering either of the unilamellar or multilamellar nanoparticles or nanostructures can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle or nanostructures. In other examples, functional groups such as antibodies and aptamers can be added to the outer surface of the membrane to enhance site targeting, such as to cell surface epitopes found in cancer cells. The membrane of the nanoparticles or nanostructures can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: In some embodiments, the term "nanoparticle" as used herein refers to nanostructure, particles, vesicles, or fragments thereof having at least one dimension (e.g., height, length, width, or diameter) of between about 1 nm and about 10 μm. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting an interior compartment (or an inner core) covered by an outer surface (or shell) comprising the membrane as discussed herein. The disclosure contemplates any nanoparticles now known and later developed that can be coated with the membrane described herein.

In some embodiment, the term "nanostructure" as used herein refers to a structure, e.g., a nanofiber, a nanotube, a nanowire, or a nanosheet, having at least one dimension (e.g., height, length, width, or diameter) of between about 1 nm and about 10 μm. A "nanostructure" can be a 1D nanostructure or a 2 D nanostructure. A dimensional parameter of a second dimension and/or a third dimension may or may not be in a dimensional range (e.g., height, length, width, or diameter) between about 1 nm and about 10 μm. The term "nanostructure" includes, but is not necessarily limited to, a nanofiber, a nanotube, a nanowire, or a nanosheet and engineered features. The nanostructure and engineered features can have, for example, a regular or irregular shape. The nanostructure can be composed of inorganic, organic materials or other materials, and can alternatively be implemented with porous materials. The layer of nanostructures can be implemented with nanostructures in a monolayer or with a layer having agglomerations of nanostructures. In some embodiments, the nanostructure has an inner core covered by an outer surface comprising a cellular derived membrane. The invention contemplates any nanostructures now known and later developed that can be coated with the membranes described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosul fates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1 ,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20$^{th}$ ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject or contacting a subject's fluid, e.g., a subject's blood, ex vivo, in view of the nature and severity of that subject's disease or condition, will have a desired therapeutic effect, e.g., an amount which will cure, prevent, inhibit, or at least partially arrest or partially prevent a target disease or condition. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. DEVICES COMPRISING A CARTRIDGE OR SORBENT COMPRISING A CELLULAR MEMBRANE

In one aspect, the present disclosure provides for a device, e.g., an extracorporeal blood purification (EBP) device, which comprises a cartridge or sorbent comprising a cellular membrane derived from a cell.

In the present devices, the cartridge or sorbent can have any suitable ratio between the surface area of the cellular membrane and the volume of the cartridge or sorbent. In some embodiments, the cartridge or sorbent can have a ratio between the surface area of the cellular membrane and the volume of the cartridge or sorbent that ranges from about 1 $m^{-1}$ to about $3 \times 10^8$ $m^{-1}$, e.g., at about 1 $m^{-1}$, 10 $m^{-1}$, 100 $m^{-1}$, 1,000 $m^{-1}$, $1 \times 10^4$ $m^{-1}$, $1 \times 10^5$ $m^{-1}$, $1 \times 10^6$ $m^{-1}$, $1 \times 10^7$ $m^{-1}$, $1 \times 10^8$ $m^{-1}$, $3 \times 10^8$ $m^{-1}$, or any subrange thereof.

In the present devices, a cartridge or sorbent can comprise a cellular membrane derived from a cell in any suitable form. For example, in the present devices, the cartridge or sorbent can comprise nanoparticles comprising the cellular membrane, nanostructures, e.g., nanofibers, comprising the cellular membrane, plenary surfaces comprising the cellular membrane, or a combination thereof.

In some embodiments, in the present devices, the cartridge or sorbent comprises nanoparticles comprising the cellular membrane. Any suitable nanoparticles can be used in the present devices. For example, in the present devices, the cartridge or sorbent can comprise a nanoparticle that comprises: a) an inner core comprising a non-cellular material; and b) an outer surface comprising a cellular membrane derived from a cell. Other suitable or exemplary nanoparticles described and/or claimed in US 2013/337066 A1 and WO 2013/052167 A2 can also be used.

In some embodiments, in the present devices, the cartridge or sorbent comprises nanostructures, e.g., nanofibers, comprising the cellular membrane. Any suitable nanostructures or nanofibers can be used in the present devices. For example, in the present devices, the cartridge or sorbent can comprise a nanostructure that comprises: a) an inner core comprising a non-cellular material; and b) an outer surface comprising a cellular membrane derived from a cell, wherein said nanostructure: 1) has a first dimension with a first dimensional parameter ranging from about 1 nm to about 10 μm and a second dimension with a second dimensional parameter of at least about 11 nm; and/or 2) has a first dimension with a first dimensional parameter ranging from about 1 nm to about 10 μm, a second dimension with a second dimensional parameter, and a ratio between said second dimensional parameter and said first dimensional parameter of at least about 2. Other suitable or exemplary nanostructures or nanofibers described and/or claimed in WO 2017/120342 A1 and Wansong Chen et al., "Coating nanofiber scaffolds with beta cell membrane to promote cell proliferation and function," *Nanoscale*, 8:10364-10370 (2016) can also be used.

In some embodiments, in the present devices, the cartridge or sorbent comprises plenary surfaces comprising the cellular membrane. The cellular membrane can be placed on the plenary surfaces in any suitable manner. For example, the cellular membrane can be coated or spread on the plenary surfaces. In another example, the cellular membrane can be placed on the plenary surfaces by the methods or processes described in Hua Gong et al., "Biomembrane-Modified Field Effect Transistors for Sensitive and Quantitative Detection of Biological Toxins and Pathogens," *ACS Nano*, 13:3714-3722 (2019).

In some embodiments, in the present devices, the cartridge or sorbent comprises at least 2 of the following: 1) nanoparticles comprising the cellular membrane; 2) nanostructures, e.g., nanofibers, comprising the cellular membrane; and 3) plenary surfaces comprising the cellular membrane. For example, in the present devices, the cartridge or sorbent can comprise: nanoparticles comprising the cellular membrane and nanostructures, e.g., nanofibers, comprising the cellular membrane; nanoparticles comprising the cellular membrane and plenary surfaces comprising the cellular membrane; or nanostructures, e.g., nanofibers, comprising the cellular membrane; and plenary surfaces comprising the cellular membrane. In some embodiments, in the present devices, the cartridge or sorbent comprises 1) nanoparticles comprising the cellular membrane; 2) nanostructures, e.g., nanofibers, comprising the cellular membrane; and 3) plenary surfaces comprising the cellular membrane.

In the present devices, the cartridge or sorbent can comprise any suitable cellular membrane. In some embodiments, in the present devices, the cartridge or sorbent can comprise plasma membrane or an intracellular membrane derived from a unicellular (e.g., a bacterium or fungus) or multicellular organism (e.g., a plant, an animal, a non-human mammal, vertebrate, or a human). In some embodiments, in the present devices, the cartridge or sorbent can comprise a naturally occurring cellular membrane, a modified cellular membrane, or a combined or fused naturally occurring cellular membrane and a modified cellular membrane. For example, in the present devices, the cartridge or sorbent can comprise a combined or fused naturally occurring cellular membrane and a modified cellular membrane, or a combined or fused naturally occurring cellular membrane and a synthetic membrane. In another example, in the present devices, the cartridge or sorbent can comprise a combined or fused naturally occurring cellular membrane, a modified cellular membrane and a synthetic membrane.

The cellular membrane can be modified in any suitable manner. For example, in the present devices, the cartridge or sorbent can comprise cellular membrane with altered or enhanced level of hormone such as cholesterol and/or altered or enhanced level of lipid such as sphingomyelin. (See e.g., US 2015/0157570 A1.) In some embodiments, in the present devices, the cartridge or sorbent can comprise a cellular membrane with altered or enhanced level of cholesterol and sphingomyelin.

In various embodiments, the cellular membrane in the present devices can be further modified to be saturated or unsaturated with other lipid components, such as cholesterol, free fatty acids, and phospholipids, also can include endogenous or added proteins and carbohydrates, such as cellular surface antigens. In such cases, an excess amount of the other lipid components can be added to the membrane wall which will shed until the concentration in the membrane wall reaches equilibrium, which can be dependent upon the nanoparticle or nanostructure environment. Membranes may also comprise other agents that may or may not increase an activity of the present devices. In other examples, functional groups such as antibodies and aptamers can be added to the outer surface of the membrane to enhance site targeting, such as to cell surface epitopes. The cellular membrane in the present devices can also comprise particles that can be biodegradable, cationic nanoparticles including, but not limited to, gold, silver, and synthetic nanoparticles. (See e.g., WO 2017/120342 A1.)

In some embodiments, in the present devices, the cartridge or sorbent comprises a cellular membrane derived from a blood cell, a tumor cell, a cancer cell, an immune cell, a stem cell, an endothelial cell, a neuronal cell, an exosome, a secretory vesicle and/or a synaptic vesicle. In some embodiments, in the present devices, the cartridge or sorbent comprises a cellular membrane derived from a red blood cell, a platelet, a macrophage, a neutrophil and/or a neuronal cell. In some embodiments, in the present devices, the cartridge or sorbent comprises a cellular membrane derived from a macrophage. In some embodiments, in the present devices, the cartridge or sorbent comprises a cellular membrane derived from a macrophage and a neutrophil. In some embodiments, in the present devices, the cartridge or sorbent comprises a cellular membrane derived from a red blood cell and a platelet. In some embodiments, in the present devices, the cartridge or sorbent comprises a cellular membrane derived from a red blood cell, a platelet and a neuronal cell.

The present devices can have any suitable dimensions, e.g., suitable length and cross-section surface area. In some embodiments, the present devices can have a length that ranges from 0.01 m to 1 m (meter), e.g., about 0.01 m, 0.02 m, 0.03 m, 0.04 m, 0.05 m, 0.06 m, 0.07 m, 0.08 m, 0.09 m, 0.1 m, 0.2 m, 0.3 m, 0.4 m, 0.5 m, 0.6 m, 0.7 m, 0.8 m, 0.9 m, 1 m, or any subrange thereof. In some embodiments, the present devices can have a cross-section surface area that ranges from $2.5 \times 1^{-5}$ m$^2$ (square meter) to about 0.01 m$^2$ (square meter), e.g., about $2.5 \times 1^{-5}$ m$^2$, $5 \times 1^{-5}$ m$^2$, $1 \times 1^{-4}$ m$^2$, $1 \times 1^{-3}$ m$^2$, 0.01 m$^2$, or any subrange thereof.

The present devices can have any suitable shape. For example, the present devices can be configured as a column, wherein the cartridge or sorbent is located or packed within a tube. In another example, the present devices can be configured as a planar device, wherein the cartridge or sorbent is present as or on a plane.

The present devices can be configured for any suitable use or purpose. For example, the present devices can be configured as an extracorporeal blood purification (EBP) device.

In the present devices, the cartridge or sorbent can comprise the cellular membranes that are derived from any suitable type(s) or number of cells. In some embodiments, in the present devices, the cartridge or sorbent comprises the cellular membrane that is derived from a single type of cell. In some embodiments, in the present devices, the cartridge or sorbent comprises the cellular membranes that are derived from different types of cells.

In another aspect, the present disclosure provides for a device assembly, which comprises at least two of the above devices, wherein the at least two devices are in fluid communication and comprise cartridges or sorbents comprising cellular membranes derived from different types of cells. For example, the present device assembly can comprise 2, 3, 4, 5, 6 7, 8, 9, 10, 15, 20, 25, 30, 40, 50 or more of the devices that are in tandem (or sequential) fluid communication.

C. METHODS FOR REMOVING OR REDUCING A SUBSTANCE FROM A LIQUID

In still another aspect, the present disclosure provides for a method for removing or reducing a substance from a liquid, e.g., a liquid obtained from a subject, which method comprises, ex vivo, contacting a liquid, e.g., a liquid obtained from a subject, with a device comprising a cellular membrane derived from a cell.

The present methods can be used for removing or reducing a substance from any suitable liquid, e.g., any suitable liquid obtained from a subject. For example, the present methods can be used for removing or reducing a substance, e.g., an undesirable substance, from a blood or urine from a subject. In some embodiments, the present disclosure provides for a method for removing or reducing a substance, e.g., an undesirable substance, from a subject's blood, which method comprises, ex vivo, contacting a subject's blood with a device comprising a cellular membrane derived from a cell.

Any suitable device or device assembly can be used in the present methods. In some embodiments, the present methods comprise contacting a liquid, e.g., a liquid, blood or urine obtained from a subject, with device or device assembly described above.

The present methods can be used for removing or reducing any suitable undesirable substance from a liquid, e.g., any suitable liquid, blood or urine obtained from a subject. For example, the present methods can be used for removing or reducing a waste product, a cytokine, e.g., a proinflammatory cytokine, and/or a toxin in a liquid, e.g., any suitable liquid, blood or urine obtained from a subject. The present methods can be used for removing or reducing any suitable types of toxin, e.g., a viral, bacterial, fungal, plant and/or animal toxin.

The present methods can be used for removing or reducing any suitable undesirable substance from a liquid of any suitable subject. For example, the subject is a mammal. In some embodiments, the mammal is a non-human mammal. In some embodiments, the mammal is a human, e.g., a human patient.

The present methods can be used for removing or reducing an undesirable substance from a liquid by a suitable or desirable degree. For example, the present methods can be used for substantially removing or reducing all substances from a subject's liquid or blood that target or attack a target cell of the subject. In some embodiments, the present methods can be used for substantially removing about at least 10%, 20%, 30%, 40%, 50%, 60%, 70%, 80%, 90%, 95%, 96%, 97%, 98%, 99%, or more of the substances from a subject's liquid or blood that target or attack a target cell of the subject. In another example, the present methods can be used for substantially removing or reducing all pathological factors or virulence factors from a subject's liquid or blood that target or attack a target cell of the subject. In some embodiments, the present methods can be used for substantially removing about at least 10%, 20%, 30%, 40%, 50%, 60%, 70%, 80%, 90%, 95%, 96%, 97%, 98%, 99%, or more of the pathological factors or virulence factors from a subject's liquid or blood that target or attack a target cell of the subject.

In some embodiments, the target cell of the subject and the cell from which the cellular membrane is derived are the same type of cell. In some embodiments, the target cell of the subject and the cell from which the cellular membrane is derived are different types of cells.

The present methods can be used for any suitable use or purpose. In some embodiments, the present method is used for hemodialysis (HD), hemofiltration (HF), hemodiafiltration (HDF) or high-flux dialysis (HFD). In some embodiments, the present method is used for treating or preventing renal failure, liver failure or sepsis in a subject. In some embodiments, the present method is used for treating or preventing infection, severe infection and/or sepsis in a subject, and wherein the cellular membrane is derived from a macrophage. In some embodiments, the present method is used for treating or preventing an inflammatory disorder or a severe inflammatory disorder, e.g., rheumatoid arthritis or pancreatitis in a subject, and wherein the cellular membrane is derived from a macrophage and/or a neutrophil. In some embodiments, the present method is used for treating or preventing an autoimmune disease, e.g., autoimmune anemia, in a subject, and wherein the cellular membrane is derived from a red blood cell and/or a platelet. In some embodiments, the present method is used for treating or preventing chemical or biological weapon attack in a subject, and wherein the cellular membrane is derived from a red blood cell, a platelet and/or a neuronal cell. In some embodiments, the present method is used for treating or preventing animal envenomation, e.g., fatal animal envenomation, in a subject, and wherein the cellular membrane is derived from a red blood cell, a platelet and/or a neuronal cell.

The present methods can use any suitable number of the device or device assembly. In some embodiments, the present methods uses a single device or device assembly. In some embodiments, the present methods uses multiple devices or a device assembly. In some embodiments, the present methods uses multiple devices or a device assembly for removing or reducing multiple substances from a liquid, e.g., a subject's liquid or blood. In some cases, each of the devices in the multiple devices or the device assembly is used for removing or reducing a particular (or a particular type) substance from a liquid, e.g., a subject's liquid or blood.

D. EXEMPLARY EMBODIMENTS

In some embodiments, the present invention uses the membrane derived from living cells as the active component to selectively capture and remove substantially all or all pathological factors or virulence factors which would otherwise attack cells for bioactivity (FIG. 1). Compared to existing techniques, membrane-based detoxification has unique advantages. (1) By selecting the membrane from different cell types, the device can be used for different diseases. (2) Cell membranes display the exact antigenic profile as the source cell. Therefore, the devices can remove toxins without the need of identifying individual toxin component. (3) By acting as the proxy of the target cells, these devices can capture toxins by precisely mapping the complexity and multiplicity of disease pathology. (4) The derivation of cell membrane from different cell types follows similar manufacturing process, which facilitates or ensures the scalability of the technique.

In some embodiments, to make membrane cartridges, cell membrane will be combined with other engineering approaches such as nanotechnology for packing into the filter/cartridge (FIG. 2). By combining with nanotechnology, the material surface-to-volume ratio will be significantly increased. This will allow a large amount of membranes to be packed into a small volume for detoxification. For example, membrane can be formulated into nanoparticles. In some cases, the nanoparticles can be either embedded into a hydrogel for retention or wrapped around magnetic particles for enrichment and isolation. Membrane can also be spread onto plenary surfaces or onto fibers that allow a fluid to pass and the toxins to be captured.

In some embodiments, for treatment, specific cell type can be selected for membrane derivation and applied to treat different diseases (See e.g., Table 1). For example, to treat severe infection and sepsis, membranes from macrophages can be used. To treat severe inflammatory disorders such as rheumatoid arthritis or pancreatitis, membranes from neutrophils can be used. To treat critical autoimmune diseases such autoimmune anemia, membrane from red blood cells (RBCs) can be used. To treat chemical & biological weapon attack or fatal animal envenomation, membranes from RBCs or neuronal cells can be used.

TABLE 1

Potential diseases that can be treated with membrane-based extracorporeal detoxification and potential membrane sources.

| Diseases | Potential Membrane Source |
| --- | --- |
| Severe infection and sepsis | Macrophages |
| Severe inflammatory disorder | Macrophages, neutrophils |
| Critical autoimmune diseases | Red blood cells, platelets |
| Chemical & biological weapon attack | Red blood cells, platelets, and neuronal cells |
| Fatal animal envenomation | Red blood cells, platelets, and neuronal cells |

In some embodiments, given the complexity of the diseases, membranes from multiple cells can be used. In this case, membrane cartridges can be serially connected, and the fluid can go through sequential detoxification (FIG. 3).

What is claimed is:

1. A device for extracorporeal detoxification, which comprises a cartridge or sorbent comprising a cellular membrane derived from a cell, and wherein said cartridge or sorbent has a ratio between a surface area of said cellular membrane and a volume of said cartridge or sorbent that ranges from about $1 \times 10^4$ $m^{-1}$ to about $3 \times 10^8$ $m^{-1}$.

2. The device of claim 1, wherein the cartridge or sorbent has a ratio between the surface area of the cellular membrane and the volume of the cartridge or sorbent that ranges from about $1 \times 10^5$ $m^{-1}$ to about $3 \times 10^8$ $m^{-1}$.

3. The device of claim 1, wherein the cartridge or sorbent comprises nanoparticles comprising the cellular membrane, nanostructures comprising the cellular membrane, plenary surfaces comprising the cellular membrane, or a combination thereof.

4. The device of claim 1, wherein the cartridge or sorbent comprises nanoparticles comprising the cellular membrane.

5. The device of claim 3, wherein the cellular membrane of the nanoparticle comprises a plasma membrane or an intracellular membrane.

6. The device of claim 3, wherein the cellular membrane of the nanoparticle is derived from a multicellular organism.

7. The device of claim 3, wherein the nanoparticle further comprises a releasable cargo.

8. The device of claim 3, wherein the nanoparticle has a diameter from about 10 nm to about 10 μm.

9. The device of claim 3, wherein the nanoparticle substantially lacks constituents of the cell from which the cellular membrane is derived.

10. The device of claim 3, wherein the nanoparticle substantially maintains natural structural integrity or activity of the cellular membrane, or the constituents of the cellular membrane.

11. The device of claim 3, the nanoparticle is biocompatible or biodegradable.

12. The device of claim 3, wherein the inner core of the nanoparticle comprises PLGA and the outer surface comprises a plasma membrane derived from a red blood cell.

13. The device of claim 3, wherein the nanoparticle substantially lacks immunogenicity to a species or subject from which the cellular membrane is derived.

14. The device of claim 3, wherein the outer surface comprises a naturally occurring cellular membrane and further comprises a modified cellular membrane and/or a synthetic membrane.

15. The device of claim 1, wherein the cartridge or sorbent comprises nanostructures comprising the cellular membrane.

16. The device of claim 1, wherein the cartridge or sorbent comprises nanofibers comprising the cellular membrane.

17. The device of claim 1, wherein the cartridge or sorbent comprises at least 2 or all 3 of the following:

1) nanoparticles comprising the cellular membrane;
   2) nanostructures comprising the cellular membrane;
   3) plenary surfaces comprising the cellular membrane.

18. The device of claim 1, wherein the cellular membrane is derived from a blood cell, a tumor cell, a cancer cell, an immune cell, a stem cell, an endothelial cell, a neuronal cell, an exosome, a secretory vesicle and/or a synaptic vesicle.

19. The device of claim 1, which has a length that ranges from 0.01 m to 1 m (meter).

20. The device of claim 1, which has a cross-section surface area that ranges from $1 \times 10^{-3}$ $m^2$ (square meter) to about 0.01 $m^2$ (square meter).

21. The device of claim 1, which is an extracorporeal blood purification (EBP) device.

22. The device of claim 1, wherein the cellular membranes are derived from different types of cells.

23. A method for removing or reducing a substance from a liquid which method comprises, ex vivo, contacting a liquid with the device of claim 1.

* * * * *